(12) United States Patent
London et al.

(10) Patent No.: US 7,236,565 B2
(45) Date of Patent: Jun. 26, 2007

(54) TAMPER TO DELAY MOTION AND DECREASE IONIZATION OF A SAMPLE DURING SHORT PULSE X-RAY IMAGING

(75) Inventors: Richard A. London, Orinda, CA (US); Abraham Szoke, Fremont, CA (US); Stefan P. Hau-Riege, Fremont, CA (US); Henry N. Chapman, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 94 days.

(21) Appl. No.: 11/134,207

(22) Filed: May 17, 2005

(65) Prior Publication Data

US 2005/0276370 A1 Dec. 15, 2005

Related U.S. Application Data

(60) Provisional application No. 60/572,875, filed on May 19, 2004.

(51) Int. Cl.
*G01N 23/04* (2006.01)
(52) U.S. Cl. .......................................... 378/62; 378/79
(58) Field of Classification Search ............ 378/70–90, 378/43, 62, 208; 435/7.1
See application file for complete search history.

(56) References Cited

U.S. PATENT DOCUMENTS

| | | | |
|---|---|---|---|
| 5,181,233 A | 1/1993 | Rink et al. | |
| 5,866,907 A | 2/1999 | Drukier et al. | |
| 6,643,353 B2 | 11/2003 | Verman et al. | |
| 6,968,037 B2 * | 11/2005 | Rosso et al. ................... | 378/79 |
| 2002/0067800 A1 * | 6/2002 | Newman et al. .............. | 378/73 |
| 2005/0074092 A1 | 4/2005 | Borgstahl et al. | |

FOREIGN PATENT DOCUMENTS

| | | |
|---|---|---|
| EP | 0 365 111 B1 | 4/1994 |
| EP | 0 581 339 B1 | 12/1999 |

OTHER PUBLICATIONS

Neutze, R., et al., "Potential for biomolecular imaging with femtosecond X-ray pulses," Nature, vol. 406, Aug. 17, 2000, pp. 752-757.

* cited by examiner

*Primary Examiner*—Edward J. Glick
*Assistant Examiner*—Hoon Song
(74) *Attorney, Agent, or Firm*—Eddie E. Scott; John H. Lee

(57) ABSTRACT

A system for x-ray imaging of a small sample comprising positioning a tamper so that it is operatively connected to the sample, directing short intense x-ray pulses onto the tamper and the sample, and detecting an image from the sample. The tamper delays the explosive motion of the sample during irradiation by the short intense x-ray pulses, thereby extending the time to obtain an x-ray image of the original structure of the sample.

57 Claims, 5 Drawing Sheets

TAMPER TO DELAY MOTION AND DECREASE IONIZATION OF A SAMPLE DURING SHORT PULSE X-RAY IMAGING

CROSS-REFERENCE TO RELATED APPLICATIONS

This application claims the benefit of U.S. Provisional Patent Application No. 60/572,875 filed May 19, 2004 by Richard A. London, Abraham Szoke, Stefan P. Hau-Riege, and Henry N. Chapman and titled "A Tamper to Delay the Motion of a Sample During Irradiation by Short Intense X-ray Pulses." U.S. Provisional Patent Application No. 60/572,875 filed May 19, 2004 is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to sample irradiation and more particularly to sample irradiation by short, intense X-ray pulses in the process of imaging the sample.

2. State of Technology

The article "Potential for Biomolecular Imaging with Femtosecond X-ray Pulses;" by Richard Neutze, Remco Wouts, David Van Der Spoel, Edgar Weckert and Janos Hajdu; in the Aug. 17, 2000 issue of NATURE (Vol. 406, pages 752–757) provides the following state of technology information: Sample damage by X-rays and other radiation limits the resolution of structural studies on non-repetitive and non-reproducible structures such as individual biomolecules or cells . . . . Radiation damage is caused by X-ray photons depositing energy directly into the sample.

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The principal tool for structure determination of biological molecules is x-ray diffraction imaging of crystals containing many identical molecules. In crystals, radiation damage is divided among the molecules, while the x-rays diffracted from individual molecules add up, resulting in a good diffraction image without damaging the crystal. Since most biological molecules have proven very difficult or as-yet impossible to crystallize, it is highly desirable to develop a method to determine structure from un-crystallized single molecules, or small "nanocrystals," which are easier to create than large crystals. However, image resolution of small biological samples is severely limited by radiation damage.

Upon irradiation by a short intense pulse of x-rays, such as one from an x-ray free electron laser, a small sample will absorb energy and ultimately be destroyed in a rapid explosion. In order to obtain a good image, the pulse length must be shorter than the time for the explosion to occur. Even with pulse lengths of x-ray free electron lasers (10–200 fs) it has been calculated that there will be unacceptable explosive motion for single molecules. Therefore, a method to delay the explosion of an x-ray irradiation sample is desired.

The present invention provides an apparatus for x-ray imaging of a small sample comprising a source of short intense x-ray pulses directed to the sample, a tamper operatively connected to the sample, and a detector. The sample can be a single molecule, multiple molecules, a biological molecule, biological molecules, a small crystal, a molecular complex, a non-biological small sample, or other sample. The tamper can be any material for which the appropriate layer can be manufactured. In general, it is desirable to use a composition containing mainly light elements so that the x-ray diffraction from the tamper material will not overwhelm that from the sample. The tamper delays the explosive motion and reduces ionization damage of the sample during irradiation by the short intense x-ray pulses, thereby extending the time to obtain an x-ray image of the original structure of the sample.

The present invention also provides a method of x-ray imaging of a small sample comprising the steps of positioning a tamper so that it is operatively connected to the sample, directing short intense x-ray pulses onto said tamper and the sample, and detecting an image from the sample. The source of short intense x-ray pulses can be an x-ray free electron laser, a synchrotron, a linac, an x-ray tube, or other sources of short intense x-ray pulses. The tamper is a layer of material that will confine the sample for the duration of an x-ray pulse, so that a good image of the sample's initial structure can be obtained.

The present invention can be used by researchers to aid in the determination of the structure of biological molecules without the need to form large crystals containing many molecules. It can be used on single molecules or small crystals. It can also be used for molecular complexes. It may be used in determining the structure of non-biological small samples in the nanometer to micrometer size scale. The present invention can be used by drug and biotechnology companies to help develop new drugs. It can also be used to determine the structures of pathogens to aid in the detection and identification of pathogens. The present invention can be used by electronics and optics industries to aid in the imaging of nanometer sized devices.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1B:
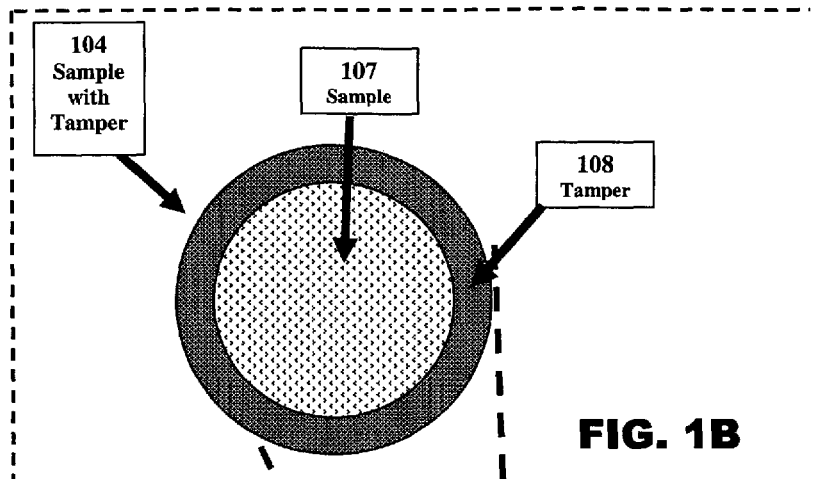
FIG. 1B shows the tamper and sample in greater detail.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

The principal tool for structure determination of biological molecules is x-ray diffraction imaging of crystals containing many identical molecules. In crystals, radiation damage is divided among the molecules, while the x-rays diffracted from individual molecules add up, resulting in a good diffraction image without damaging the crystal. Since most biological molecules have proven very difficult or as-yet impossible to crystallize, it is highly desirable to develop a method to determine structure from un-crystallized single molecules, or small "nanocrystals," which are easier to create than large crystals. However, image resolution of small biological samples is severely limited by radiation damage.

Upon irradiation by a short intense pulse of x-rays, such as one from an x-ray free electron laser, a small sample will absorb energy and ultimately be destroyed in a rapid explosion. In order to obtain a good image, the pulse length must be shorter than the time for the explosion to occur. Even with pulse lengths of x-ray free electron lasers (10–200 fs) it has been calculated that there will be unacceptable explosive motion for single molecules. Therefore, a method to delay the explosion of an x-ray irradiation sample is desired.

Figure 1A:
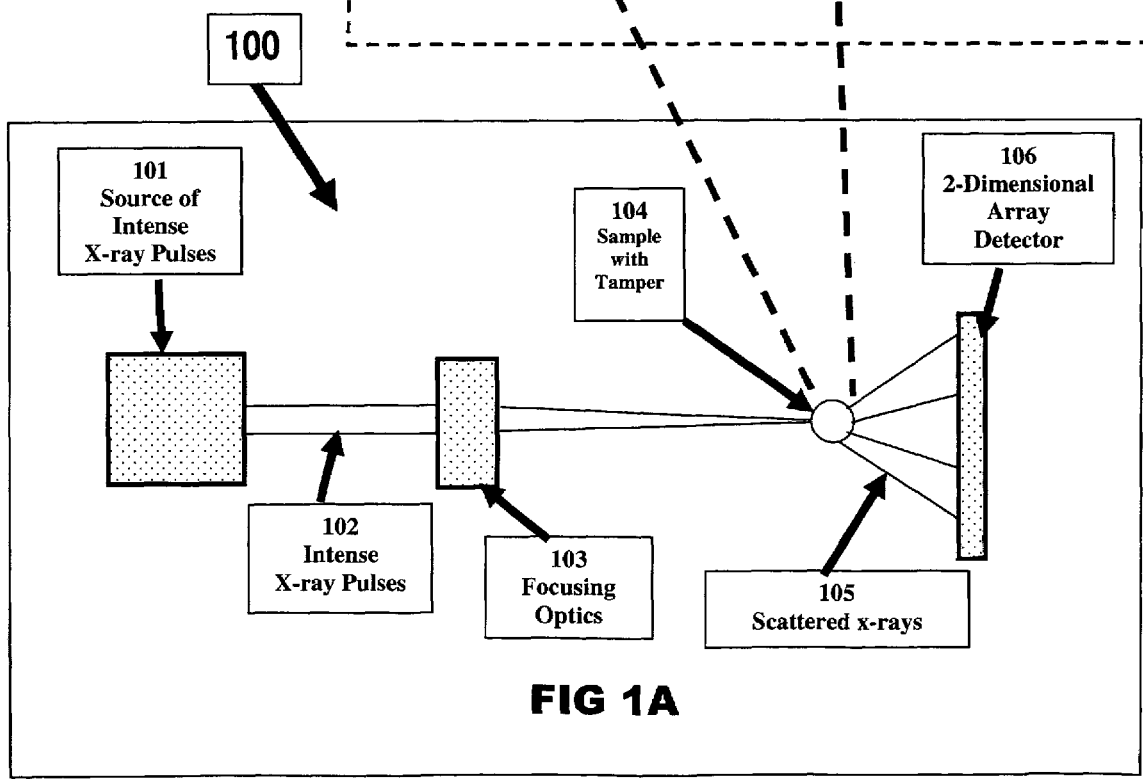
FIG. 1A illustrates a system for x-ray imaging of small samples.

Referring now to the drawings and in particular to FIGS. 1A and 1B, a system for x-ray imaging of small samples is illustrated. The system is designated generally by the reference numeral 100. As illustrated in FIG. 1A, the system 100 includes: a source 101 of short intense x-ray pulses 102, a system 103 for focusing the x-rays 102, and a detector 106. The source 101 produces the intense x-ray pulses 102 that are directed onto a tamped-sample 104. The tamped-sample 104 comprising the sample 107 and tamper 108 is shown in greater detail in FIG. 1B. The tamped-sample 104 scatters the x-rays producing scatter x-rays 105. The scattered x-rays 105 are recorded by a two-dimensional array detector 106. The source of short intense x-ray pulses 101 can be any source of short intense x-ray pulses. For example, the source of short intense x-ray pulses 101 can be an x-ray free electron laser, a linac, a linac in conjunction with a short pulse laser, or another source of short intense x-ray pulses. The sample 107 can be any sample to be analyzed. For example, the sample 107 can be a single molecule, multiple molecules, a biological molecule, biological molecules, a small crystal, a molecular complex, a non-biological small sample, or other sample.

The system 100 can be used by drug and biotechnology companies to help develop new drugs. It can also be used to determine the structures of pathogens to aid in the detection and identification of pathogens. The system 100 can be used by electronics and optics industries to aid in the imaging of nanometer sized devices.

Referring now to FIG. 1B, the tamped-sample 104 is shown in greater detail. The sample 107 is surrounded with a layer of material 108 that will confine the sample 107 and reduce its ionization for the duration of an x-ray pulse, so that a good image of the sample's initial structure can be obtained. The surrounding layer 108 is called a tamper. In one embodiment, the thickness of the tamper 108 need only be of order of 1 nanometer. One natural material of which to make the tamper 108 is water, since most biological molecular entities naturally occur in an aqueous environment.

In the embodiment of the present invention illustrated in FIG. 1B, the sample 107 comprises a single molecule. The thin layer of material 108 surrounds the small sample 107. The layer 108 serves as a tamper, which delays the explosive motion and reduces the ionization of the sample 107 during irradiation by a short intense pulse of x-rays, thereby extending the time to obtain an x-ray image of the original structure of the sample.

FIG. 1B shows one configuration of the tamper 108 relative to the sample 107. In this configuration the sample 107 is depicted as being nearly spherical in shape. The spherical depiction of the sample 107 in FIG. 1B is an idealization. Some real samples for which the system 100 may be used are approximately spherical in shape. Other samples may be highly non-spherical. The tamper 108 shown in FIG. 1b is thin layer of nearly constant thickness surrounding the sample molecule 107. Other configurations of the tamper 108 are used in other embodiments of the present invention. The sample 107 can be a single molecule, multiple molecules, a biological molecule, biological molecules, a small crystal, a molecular complex, a non-biological small sample, or other sample.

The composition of the tamper 108 can be any material for which the appropriate layer can be manufactured. It is desirable to use a composition containing mainly light elements so that the x-ray diffraction from the tamper material will not overwhelm that from the sample. A lot of x-ray diffraction from the tamper would make it hard to accurately measure the diffraction image of the sample.

In the system illustrated in FIG. 1B, the tamper material 108 is water. Since most biological samples naturally exist in a water environment, the structure of the sample will likely be unaltered by a layer of water. In fact, for protein molecules, a small amount of water may be necessary to obtain the correct structure relevant to a living organism. Since most biological samples are hydroscopic, the tamped sample is produce by simple wetting. In another embodiment of the present invention, the tamper 108 composition is hydrogen. In the case of the tamper 108 being hydrogen, the tamped-sample 104 must be cooled below the boiling temperature of hydrogen at 20 K. A wetting procedure to create the tamper is also used for hydrogen. Hydrogen has an advantage over water in that it generates much less x-ray diffraction. In another embodiment of the present invention, the tamper 108 composition is helium. In the case of the tamper 108 being helium, the tamped-sample 104 must be cooled below the boiling temperature of helium at 4 K. A wetting procedure to create the tamper is also used for helium. Helium has an advantage over water in that it generates much less x-ray diffraction. The tamper 108 materials of water, hydrogen, and helium are only examples. Other materials can be used without changing the essence of the present invention.

In the system illustrated in FIGS. 1A and 1B, the tamper 108 is prepared by spraying particles or molecules out from a solution. This can be achieved by electrospray, whereby a high voltage is placed on a narrow-bore capillary that is placed in the solution. By controlling the pressure differential across the capillary and the voltage, drops of precise and controllable size can be made. As the drop is passed into vacuum (e.g., through a series of skimmer apertures) the solution will tend to evaporate and reduce further in size until it is frozen. The concentration of particles in the solution is chosen so that most drops contain one particle. The drops are sent directly to the experiment interaction region, or passed through a mass spectrometer to select only those drops of a given mass (e.g., those with one particle as opposed to those with none or more than one particle).

Figure 2:
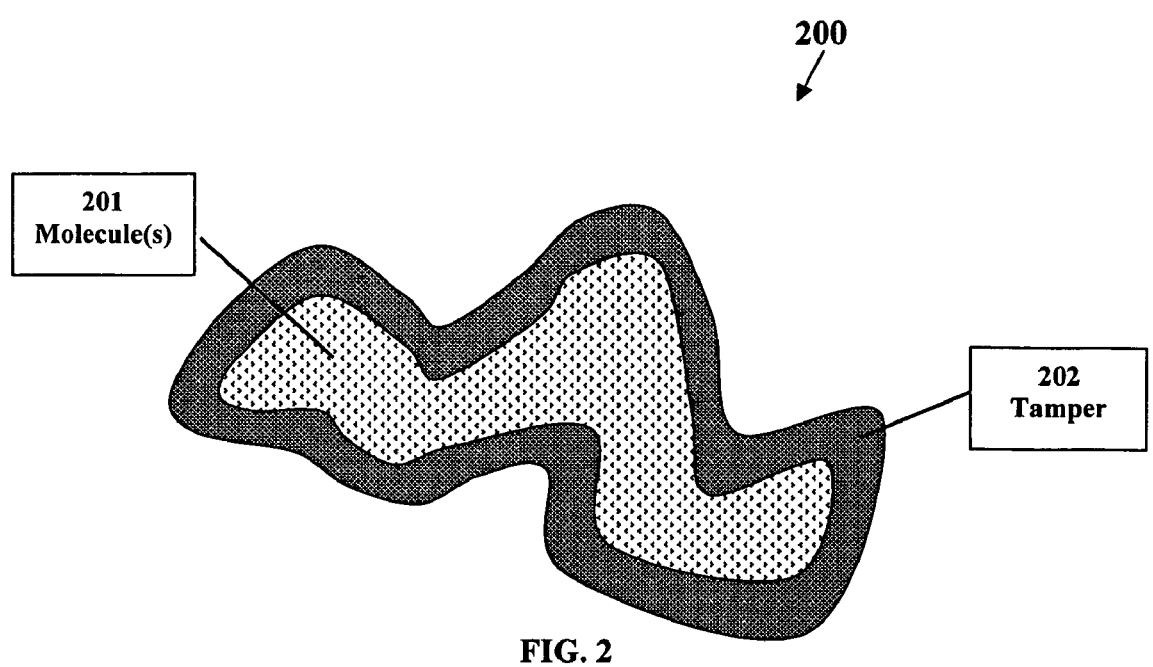
FIG. 2 illustrates another embodiment and configuration of a sample and a tamper.

Referring now to FIG. 2 another embodiment and configuration of a sample and a tamper is illustrated. This embodiment and configuration is designated generally by the reference numeral 200. As illustrated in FIG. 2, the embodiment and configuration 200 includes a sample 201 and a thin layer of material 202 surrounding the small sample 201. The layer 202 serves as a tamper, which delays the explosive motion and reduces the ionization of the sample 201 during irradiation by a short intense pulse of x-rays, thereby extending the time to obtain an x-ray image of the original structure of the sample. In the embodiment and configuration 200, the sample 201 is depicted as being irregular in shape. The tamper 202 is a thin layer of nearly constant thickness, which hugs the shape of the sample.

Figure 3:
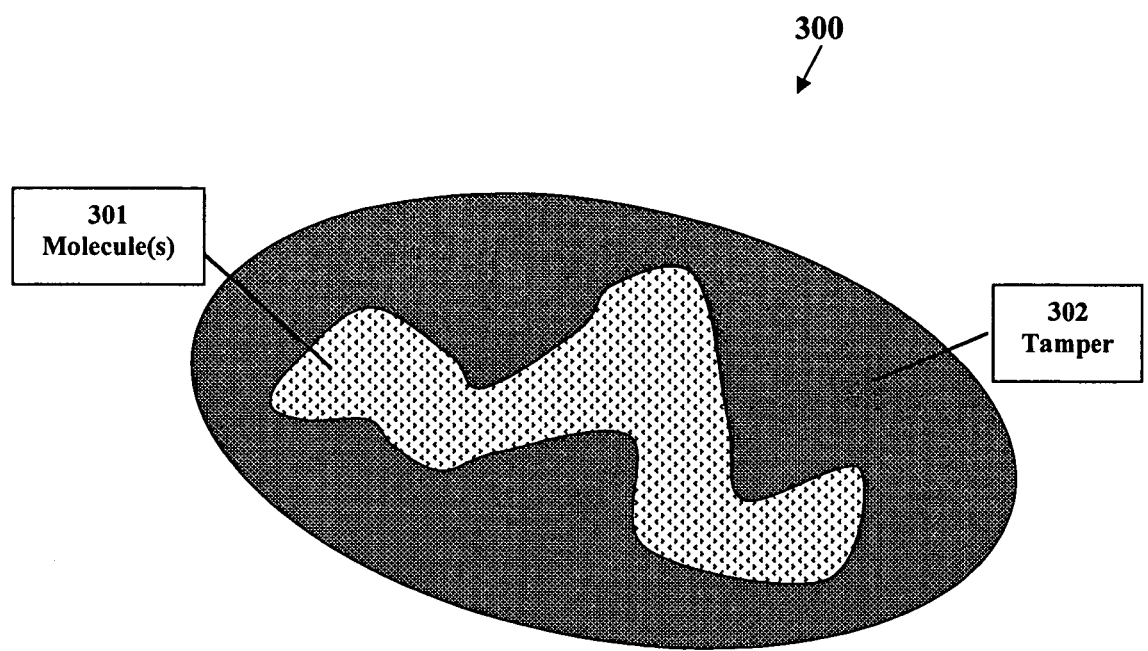
FIG. 3 illustrates yet another embodiment and configuration of a sample and a tamper.

Referring now to FIG. 3 another embodiment and configuration of a sample and a tamper is illustrated. This embodiment and configuration is designated generally by the reference numeral 300. As illustrated in FIG. 3, the embodiment and configuration 300 includes a sample 301 and a thin layer of material 302 surrounding the small sample 301. The layer 302 serves as a tamper, which delays the explosive motion and reduces the ionization of the sample 301 during irradiation by a short intense pulse of x-rays, thereby extending the time to obtain an x-ray image of the original structure of the sample. In the embodiment and configuration 300, the sample 301 is depicted as the same irregular shape as in FIG. 2, but the tamper 302 has a regular, ellipsoidal, outer shape. Such a configuration may be realized by using a liquid tamper material that has a high surface tension.

Figure 4:
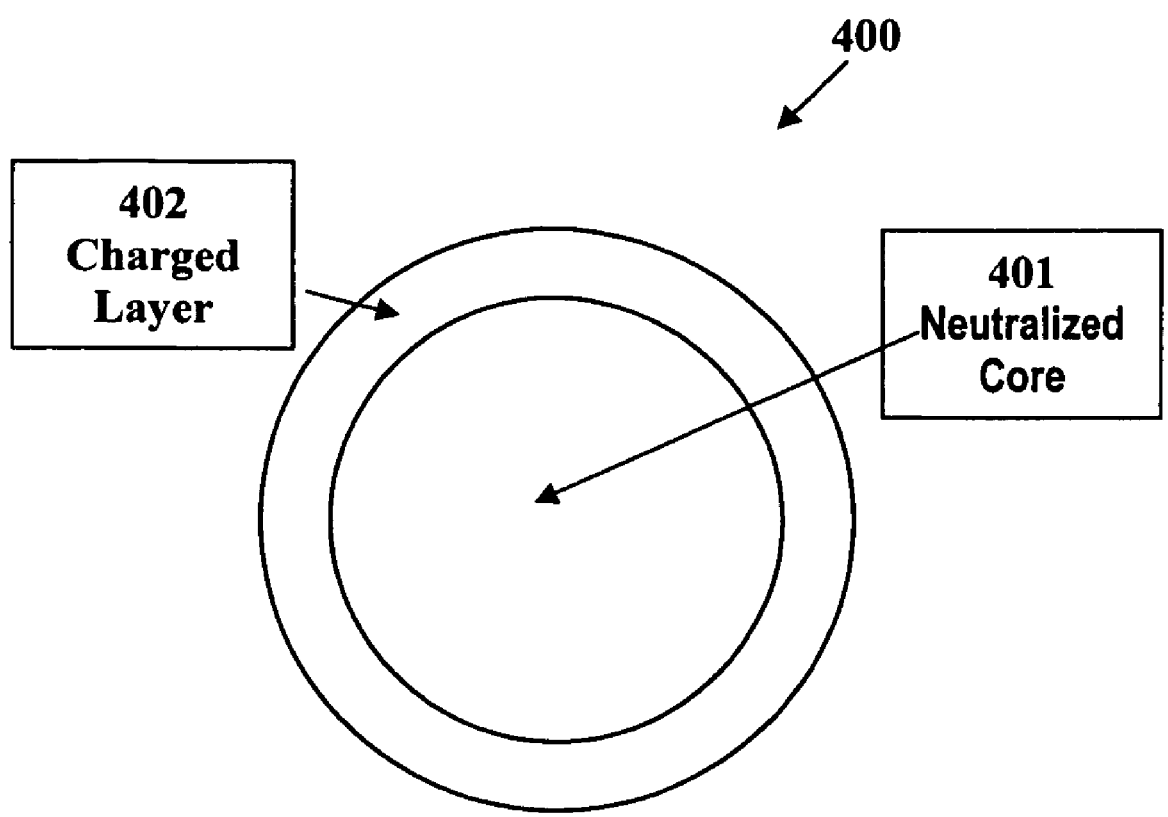
FIG. 4 illustrates additional details of a small sample.

Referring now to FIG. 4, additional details of the small sample are illustrated. The sample is designated generally by the reference numeral 400. Upon irradiation by a short pulse of x-rays used for imaging, the sample 400 will assume a two-region structure with a neutralized core 401 and a highly charge outer layer 402. Upon irradiation by a short intense pulse of x-rays, the sample will explode. The highly charged outer layer 402 will explode very quickly due to the Coulomb forces. Because of the charge neutralization, the explosion of the inner core 401 will be much slower.

For imaging biological samples at atomic resolution (approximately 0.1–0.5 nm), typical x-ray energies are 10 keV, pulses are in the range 1–20 fs, and x-ray fluences are in the range of $10^{11}$ to $10^{13}$ photons/(100 nm)$^2$. Samples are typically 1 to 1,000 nm in radius. The explosion is called a "Coulomb explosion" since the driving force is the Coulomb (or electrostatic) force due to the positive charge remaining on the sample after x-ray generated photo-electrons escape from the sample. In addition to the high-energy photoelectrons, secondary electrons are created by Auger decay of the ionized atoms and by collisional ionization by the photo- and Auger electrons. Most of the secondary electrons are trapped in the sample 400 by the positive charge left by the escaping photoelectrons. The secondary electrons will accumulate towards the center of the sample 401, screening the positive charge in that region. The outer layers 402 of the sample 400 will retain the net positive charge of magnitude equal to that of the escaped electrons. The sample 400 will therefore assume the two-region structure with a neutralized core 401 and a highly charge outer layer 402, as shown in FIG. 4.

The highly charged outer layer 402 will explode very quickly due to the Coulomb forces. Because of the charge neutralization, the explosion of the inner core 401 will be much slower. It will not experience the rapid Coulomb explosion, but rather a slower hydrodynamic rarefaction.

Figure 5:
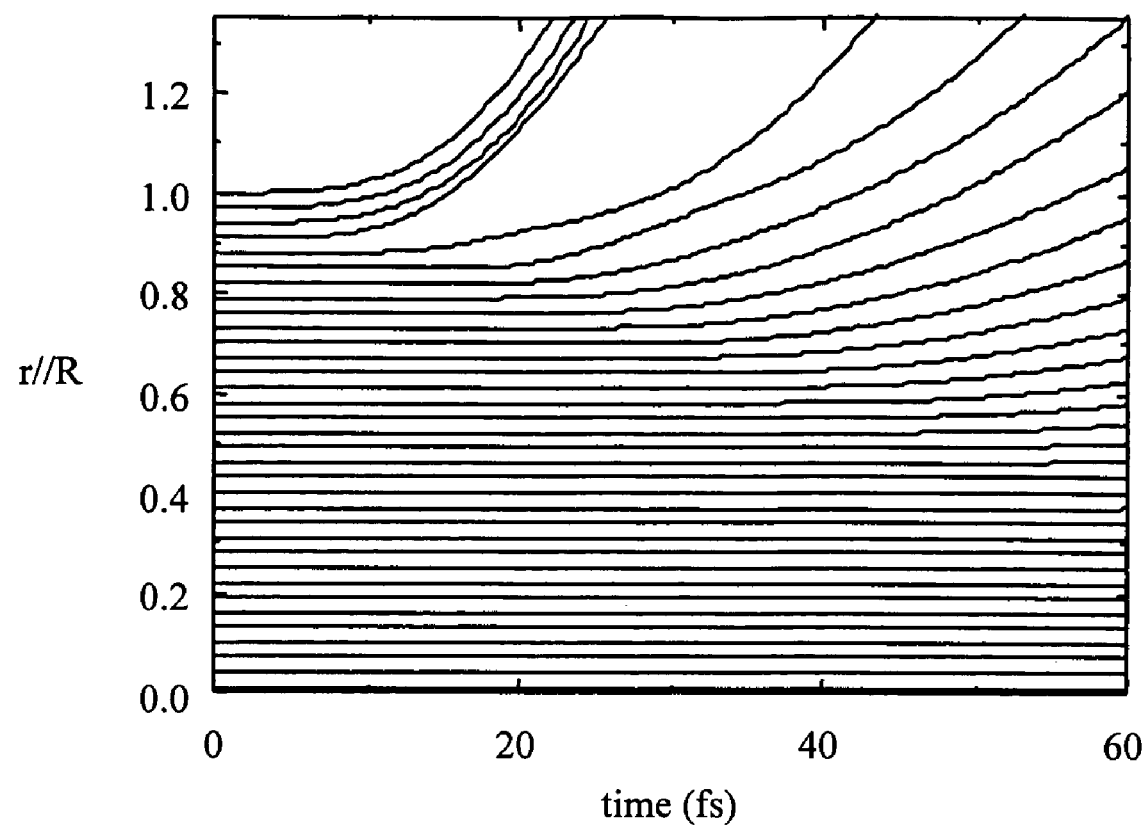
FIG. 5 is a plot of the position of Lagrangian markers versus time.

Referring now to FIG. 5, the explosion is illustrated by a plot of the position of Lagrangian markers versus time. Lagrangian markers are imaginary markers, initially placed at equal intervals of radius in the molecule, which follow the movement of the material as the molecule explodes. The trajectory of a Lagrangian marker is similar to the trajectory that an individual atom would follow in the explosion. The curves shown in FIG. 5 have been calculated with a computational model for dynamics of an x-ray irradiated sample as described in the publication: Dynamics of biological molecules irradiated by short x-ray pulses, Stefan P. Hau-Riege, Richard A. London, and Abraham Szoke, S. P. Hau-Riege, R. A. London, and A. Szoke, Physical Review E, 69, 051906 (2004).

As shown in FIG. 5, the outer 5% of the radius of the particle expands very rapidly. This is the region in which all of the net positive charge resides. The inner region is nearly charge neutral and it expands much more slowly. The tamper adds a thin layer of material, slightly larger than the rapidly expanding charged layer. As in a simulation, the tamper will contribute electrons to neutralize the molecule on the inside. The tamper will explode rapidly, but the molecule will explode more slowly.

The correct thickness of the tamper depends on several parameters: the size and composition of the sample, the wavelength, intensity and pulse length of the x-ray pulse and the composition of the tamper. The correct thickness can be estimated from an analytic formula applied to spherical molecules, or calculated more accurately with numerical simulations. The analytic formula gives the thickness of the tamper as $\Delta R = 1.2\{1-[b/(1+b)]^{-1/3}\}R$, where R is the initial radius of the sample and b is the ratio of the number of trapped electrons in the molecule to the number of escaped electrons. The factor of 1.2 in front of the formula makes the tamper slightly thicker than the charged layer thus providing a margin of error in protecting the sample from rapid expansion. The value of b has been estimated to be between 1 and 10 for biological samples of radius between 20 to 1000 Å. Thus the thickness of the tamper is estimated to lie between 3.7% and 25% of the radius of the sample. Both the analytical estimates and numerical calculations of the tamper thickness are presented only as examples. In practice, the thickness of the tamper may be different from these suggested values.

The composition of the tamper can be any material for which the appropriate layer can be manufactured. In general, it is desirable to use a composition containing mainly light elements so that the x-ray diffraction from the tamper material will not overwhelm that from the sample. A lot of x-ray diffraction from the tamper would make it hard to accurately measure the diffraction image of the sample.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus for x-ray imaging of a small sample, comprising:
a source of short intense x-ray pulses directed to the sample,
a tamper operatively connected to the sample wherein said tamper comprises a layer of material that surrounds the sample wherein said layer of material has a thickness determined by the size and composition of the sample, the wavelength, intensity and pulse length of the x-ray pulse and the composition of material, and
a detector.

2. The apparatus for x-ray imaging of a small sample of claim 1 wherein said source of short intense x-ray pulses is an x-ray free electron laser.

3. The apparatus for x-ray imaging of a small sample of claim 1 wherein said tamper is water.

4. The apparatus for x-ray imaging of a small sample of claim 1 wherein said tamper is hydrogen.

5. The apparatus for x-ray imaging of a small sample of claim 1 wherein said tamper is helium.

6. The apparatus for x-ray imaging of a small sample of claim 1 wherein said tamper has a thickness of the order of 1 nanometer.

7. The apparatus for x-ray imaging of a small sample of claim 1 wherein said tamper comprises a layer of material that surrounds a sample that is approximately spherical in shape.

8. The apparatus for x-ray imaging of a small sample of claim 1 wherein said tamper comprises a thin layer of nearly constant thickness, which hugs the shape of the sample.

9. The apparatus for x-ray imaging of a small sample of claim 1 wherein said tamper comprises a liquid tamper material that has a high surface tension.

10. The apparatus for x-ray imaging of a small sample of claim 1 wherein said tamper comprises a layer of material that surrounds a sample that is a single molecule.

11. The apparatus for x-ray imaging of a small sample of claim 1 wherein said tamper comprises a layer of material that surrounds a sample that comprises multiple molecules.

12. The apparatus for x-ray imaging of a small sample of claim 1 wherein said tamper comprises a layer of material that surrounds a sample that is a biological molecule.

13. The apparatus for x-ray imaging of a small sample of claim 1 wherein said tamper comprises a layer of material that surrounds a sample that comprises multiple biological molecules.

14. The apparatus for x-ray imaging of a small sample of claim 1 wherein said tamper comprises a layer of material that surrounds a sample that is a non-biological sample.

15. The apparatus for x-ray imaging of a small sample of claim 1 wherein said tamper comprises a layer of material that surrounds a sample that is a small crystal.

16. The apparatus for x-ray imaging of a small sample of claim 1 wherein said tamper comprises a layer of material that surrounds a sample that is a molecular complex.

17. The apparatus for x-ray imaging of a small sample of claim 1 wherein said tamper comprises a layer of material that surrounds the sample wherein said layer of material has a thickness determined by the analytic formula $\Delta R = 1.2\{1-[b/(1+b)]-\frac{1}{3}\}R$, where R is the initial radius of the sample and b is the ratio of the number of trapped electrons in the molecule to the number of escaped electrons.

18. The apparatus for x-ray imaging of a small sample of claim 1 wherein the sample has a radius and wherein said tamper has a thickness of between 3.7% and 25% of said radius of the sample.

19. An apparatus for x-ray imaging of a small sample, comprising:
source means for directing short intense x-ray pulses to the sample,
tamper means operatively connected to the sample for delaying the explosive motion and reducing the ionization of the sample during irradiation by said short intense x-ray pulse wherein said tamper means comprises a layer of material that surrounds the sample wherein said layer of material has a thickness determined by the size and composition of the sample, the wavelength, intensity and pulse length of the x-ray pulse and the composition of material, and
detector means for detecting an image from the sample.

20. The apparatus for x-ray imaging of a small sample of claim 19 wherein said source means is a x-ray free electron laser.

21. The apparatus for x-ray imaging of a small sample of claim 19 wherein said tamper means is water.

22. The apparatus for x-ray imaging of a small sample of claim 19 wherein said tamper means is hydrogen.

23. The apparatus for x-ray imaging of a small sample of claim 19 wherein said tamper is helium.

24. The apparatus for x-ray imaging of a small sample of claim 19 wherein said tamper means has a thickness of the order of 1 nanometer.

25. The apparatus for x-ray imaging of a small sample of claim 19 wherein said tamper means comprises a layer of material that surrounds a sample that is approximately spherical in shape.

26. The apparatus for x-ray imaging of a small sample of claim 19 wherein said tamper means comprises a thin layer of nearly constant thickness, which hugs the shape of the sample.

27. The apparatus for x-ray imaging of a small sample of claim 19 wherein said tamper means comprises a liquid tamper material that has a high surface tension.

28. The apparatus for x-ray imaging of a small sample of claim 19 wherein said tamper means comprises a layer of material that surrounds a sample that is a single molecule.

29. The apparatus for x-ray imaging of a small sample of claim 19 wherein said tamper means comprises a layer of material that surrounds a sample that comprises multiple molecules.

30. The apparatus for x-ray imaging of a small sample of claim 19 wherein said tamper means comprises a layer of material that surrounds a sample that is a biological molecule.

31. The apparatus for x-ray imaging of a small sample of claim 19 wherein said tamper means comprises a layer of material that surrounds a sample that comprises multiple biological molecules.

32. The apparatus for x-ray imaging of a small sample of claim 19 wherein said tamper means comprises a layer of material that surrounds a sample that is a non-biological sample.

33. The apparatus for x-ray imaging of a small sample of claim 19 wherein said tamper means comprises a layer of material that surrounds a sample that is a small crystal.

34. The apparatus for x-ray imaging of a small sample of claim 19 wherein said tamper means comprises a layer of material that surrounds a sample that is a molecular complex.

35. The apparatus for x-ray imaging of a small sample of claim 19 wherein said tamper means comprises a layer of material that surrounds the sample wherein said layer of material has a thickness determined by the analytic formula $\Delta R=1.2\{1-[b/(1+b)]-\frac{1}{3}\}R$, where R is the initial radius of the sample and b is the ratio of the number of trapped electrons in the molecule to the number of escaped electrons.

36. The apparatus for x-ray imaging of a small sample of claim 19 wherein the sample has a radius and wherein said tamper means has a thickness of between 3.7% and 25% of said radius of the sample.

37. A method of x-ray imaging of a small sample, comprising the steps of:
positioning a tamper so that it is operatively connected to the sample wherein said step of positioning a tamper so that it is operatively connected to the sample comprises positioning a layer of material around a sample at a thickness determined by the size and composition of the sample, the wavelength, intensity and pulse length of the x-ray pulse and the composition of material,
directing short intense x-ray pulses onto said tamper and the sample, and
detecting an image from the sample.

38. The method for x-ray imaging of a small sample of claim 37 wherein said step of directing short intense x-ray pulses onto said tamper and the sample comprises directing x-ray free electron laser pulses onto said tamper and the sample.

39. The method for x-ray imaging of a small sample of claim 37 wherein said step of positioning a tamper so that it is operatively connected to the sample comprises positioning a water tamper so that it is operatively connected to the sample.

40. The method for x-ray imaging of a small sample of claim 37 wherein said step of positioning a tamper so that it is operatively connected to the sample comprises positioning a water tamper so that it is operatively connected to the sample by wetting said water tamper on the sample.

41. The method for x-ray imaging of a small sample of claim 37 wherein said step of positioning a tamper so that it is operatively connected to the sample comprises positioning a hydrogen tamper so that it is operatively connected to the sample.

42. The method for x-ray imaging of a small sample of claim 37 wherein said step of positioning a tamper so that it is operatively connected to the sample comprises positioning a helium tamper so that it is operatively connected to the sample by wetting said helium tamper on the sample.

43. The method for x-ray imaging of a small sample of claim 37 wherein said step of positioning a tamper so that it is operatively connected to the sample comprises positioning a hydrogen tamper so that it is operatively connected to the sample by wetting said hydrogen tamper on the sample.

44. The method for x-ray imaging of a small sample of claim 37 wherein said step of positioning a tamper so that it is operatively connected to the sample comprises positioning a tamper that has a thickness of the order of 1 nanometer so that it is operatively connected to the sample.

45. The method for x-ray imaging of a small sample of claim 37 wherein said step of positioning a tamper so that it is operatively connected to the sample comprises positioning a layer of material around a sample that is approximately spherical in shape.

46. The method for x-ray imaging of a small sample of claim 37 wherein said step of positioning a tamper so that it is operatively connected to the sample comprises positioning a thin layer of nearly constant thickness around the sample.

47. The method for x-ray imaging of a small sample of claim 37 wherein said step of positioning a tamper so that it is operatively connected to the sample comprises positioning a liquid tamper material that has a high surface tension around the sample.

48. The method for x-ray imaging of a small sample of claim 37 wherein said step of positioning a tamper so that it is operatively connected to the sample comprises positioning a layer of material around a sample that is a single molecule.

49. The method for x-ray imaging of a small sample of claim 37 wherein said step of positioning a tamper so that it is operatively connected to the sample comprises positioning a layer of material around a sample that comprises multiple molecules.

50. The method for x-ray imaging of a small sample of claim 37 wherein said step of positioning a tamper so that it is operatively connected to the sample comprises positioning a layer of material around a sample that is a biological molecule.

51. The method for x-ray imaging of a small sample of claim 37 wherein said step of positioning a tamper so that it is operatively connected to the sample comprises positioning a layer of material around a sample that comprises multiple biological molecules.

52. The method for x-ray imaging of a small sample of claim 37 wherein said step of positioning a tamper so that it is operatively connected to the sample comprises positioning a layer of material around a sample that is a non-biological sample.

53. The method for x-ray imaging of a small sample of claim 37 wherein said step of positioning a tamper so that it is operatively connected to the sample comprises positioning a layer of material around a sample that is a small crystal.

54. The method for x-ray imaging of a small sample of claim 37 wherein said step of positioning a tamper so that it is operatively connected to the sample comprises positioning a layer of material around a sample that is a molecular complex.

55. The method for x-ray imaging of a small sample of claim 37 wherein said step of positioning a tamper so that it is operatively connected to the sample comprises positioning a layer of material around a sample that comprises a two-region structure with a neutralized core and a highly charge outer layer wherein said highly charged outer layer will explode very quickly due to Coulomb forces and said inner core will explode much slower because of charge neutralization.

56. The method for x-ray imaging of a small sample of claim 37 wherein said step of positioning a tamper so that it is operatively connected to the sample comprises positioning a layer of material around a sample at a thickness determined by the analytic formula $\Delta R=1.2\{1-[b/(1+b)]-\frac{1}{3}\}R$, where R is the initial radius of the sample and b is the ratio of the number of trapped electrons in the molecule to the number of escaped electrons.

57. The method for x-ray imaging of a small sample of claim 37 wherein said sample has a radius and wherein said step of positioning a tamper so that it is operatively connected to the sample comprises positioning a layer of material around a sample at a thickness of between 3.7% and 25% of said radius of the sample.

* * * * *